(12) United States Patent
Keane (10) Patent No.: US 12,084,700 B2
(45) Date of Patent: Sep. 10, 2024

(54) YARN REINFORCED BACTERIAL CELLULOSE HYBRID MATERIALS

(71) Applicant: Modern Synthesis Ltd., England (GB)

(72) Inventor: Jennifer K. Keane, La Jolla, CA (US)

(73) Assignee: Modern Synthesis Ltd., London (GB)

( * ) Notice: Subject to any disclaimer, the term of this patent is extended or adjusted under 35 U.S.C. 154(b) by 1105 days.

(21) Appl. No.: 16/919,240

(22) Filed: Jul. 2, 2020

(65) Prior Publication Data

US 2020/0332327 A1  Oct. 22, 2020

Related U.S. Application Data

(63) Continuation of application No. PCT/US2019/012001, filed on Jan. 1, 2019.

(30) Foreign Application Priority Data

Jan. 2, 2018 (GB) .................................. 1800027

(51) Int. Cl.
| | | |
|---|---|---|
| *C12P 19/04* | (2006.01) | |
| *C12M 1/12* | (2006.01) | |
| *D06M 16/00* | (2006.01) | |
| *D06M 101/06* | (2006.01) | |

(52) U.S. Cl.
CPC ............. *C12P 19/04* (2013.01); *C12M 25/00* (2013.01); *D06M 16/003* (2013.01); *D06M 2101/06* (2013.01)

(58) Field of Classification Search
CPC ..... C12P 19/04; C12M 25/00; D06M 16/003; D06M 2101/06
See application file for complete search history.

(56) References Cited

U.S. PATENT DOCUMENTS

| | | |
|---|---|---|
| 4,378,431 A | 3/1983 | Brown, Jr. |
| 4,912,049 A | 3/1990 | Farah |
| 5,955,326 A | 9/1999 | Bungay, III et al. |
| 6,451,032 B1 | 9/2002 | Ory et al. |
| 9,510,928 B2 | 12/2016 | Bayon et al. |
| 2007/0128243 A1 | 6/2007 | Serafica et al. |

(Continued)

FOREIGN PATENT DOCUMENTS

| | | | |
|---|---|---|---|
| CN | 103480028 A | * | 1/2014 |
| WO | 2010052586 A1 | | 5/2010 |

(Continued)

OTHER PUBLICATIONS

Complete Textile Glossary, "Knitting," Celanese Acetate (2001) (Year: 2001).*

(Continued)

*Primary Examiner* — Jeremy R Pierce
(74) *Attorney, Agent, or Firm* — LaBatt, LLC (57) ABSTRACT

A yarn reinforced bacterial cellulose hybrid composition includes a two-dimensional yarn mesh stretched and embedded within a BC sheet. Such materials are fabricated by providing a bacterial cellulose-producing bacterium; providing a suitable bacteria nutritional medium; culturing the bacterium in the nutritional medium under conditions to produce bacterial cellulose; and providing a two-dimensional yarn mesh having a defined pattern such that the yarn mesh is embedded within the bacterial cellulose.

20 Claims, 8 Drawing Sheets

(56) References Cited

U.S. PATENT DOCUMENTS

| | | | |
|---|---|---|---|
| 2008/0175980 A1* | 7/2008 | Sun | B05D 7/22 |
| | | | 427/2.25 |
| 2011/0206928 A1 | 8/2011 | Maranchi et al. | |
| 2011/0262521 A1* | 10/2011 | Bayon | A61L 27/48 |
| | | | 424/443 |
| 2019/0127907 A1* | 5/2019 | Eryilmaz | D06N 3/0088 |

FOREIGN PATENT DOCUMENTS

| | | |
|---|---|---|
| WO | 2010135234 A2 | 11/2010 |
| WO | 2016083351 A1 | 6/2016 |

OTHER PUBLICATIONS

Zhong, English translation of CN-103480028-A obtained from PE2E database (Year: 2014).*

Qiu et al., In Situ Produced Bacterial Cellulose Nanofiber-Based Hybrids for Nanocomposites, Fibers 2017, 5, 31, 10 pages.

Michael Florea et al., Engineering control of bacterial cellulose production using a genetic toolkit and a new celluloseproducing strain, Proceedings of the National Academy of Sciences of the United States of America, May 31, 2016; 113 (24) E3431-E3440, 10 pages.

Sun Hwa Lee, International Preliminary Report on Patentability, PCT/US2019/012001, Jul. 7, 2020, 13 pages.

Machine-generated translation of CN Patent Application Publication No. 103480038A acquired from the European Patent Office on Apr. 19, 2024, 12 pages.

* cited by examiner

YARN REINFORCED BACTERIAL CELLULOSE HYBRID MATERIALS

REFERENCE TO RELATED APPLICATIONS

The current application is a continuation of International Application No. PCT/US2019/012001, filed on 1 Jan. 2019, which claims the benefit of United Kingdom Patent Application No. 1800027.3, filed on 2 Jan. 2018, each of which is hereby incorporated by reference.

FIELD OF INVENTION

This invention relates to bio based materials and composites, in particular to bacterial cellulose (BC) based hybrid BC-textile materials, produced using an in situ self-assembly method.

BACKGROUND

Bacterial cellulose (BC) fibers secreted by bacterial cellulose producing bacterium such as *Komagataeibacter rhaeticus*, display many interesting characteristics including a high crystallinity, as well as high strength and stiffness (Young's modulus). BC membranes produced through static fermentation have a highly porous structure, excellent biocompatibility and are completely biodegradable. Because of their unique properties, bacterial cellulose membranes are already used in numerous industrial applications such as foods, speaker diaphragms, high quality paper, textiles, artificial skin and blood vessels, as well as a binding agent for fibers and other materials.

It has also been shown that incorporation of fibers, such as sisal fibers, into the fermentation media in self-assembly approach can produce a hybrid (i.e., composite) material with better tensile properties compared with pure BC or sisal fibers (Qui, K.; Netravali, A. In Situ Produced Bacterial Cellulose Nanofiber-Based Hybrids for Nanocomposites. Fibers 2017, 5, 31). BC materials produced so far still had limited applications. Further improvement and versatility is, therefore, needed for BC materials to achieve their potential in key industries.

SUMMARY OF INVENTION

The invention builds and improves on this knowledge to create a new type of BC-textile hybrid material.

The invention provides a composition comprising bacterial cellulose (BC) and a fiber, such as yarn, fixed in a pattern (e.g., a mesh), wherein the fiber is interwoven with (e.g., embedded within) the BC.

A method for producing bacterial cellulose (BC) based hybrid BC-textile materials is also provided comprising the steps of: providing a bacterium capable of producing cellulose; culturing the bacterium in a suitable medium in a suitable container under conditions to produce BC; providing a fiber or combination or fibers in a pattern and providing conditions wherein the fiber or combination of fibers is interwoven with the bacterial cellulose (BC).

The hybrid material produced retains the fiber/yarns in a predefined order and direction with bacterial cellulose acting as a binder. The hybrid BC-textile material thus offers much possibility for customization and engineering of aesthetic, mechanical and other material properties.

The invention can be employed across multiple product types in multiple industries and offers the possibility of products to be produced to shape, in or close to their final form.

The invention also provides an article of footwear, clothing, and/or wearable accessory comprising a Bacterial Cellulose (BC) hybrid material wherein a fiber fixed in a pattern is interwoven with the BC.

The natural biocompatibility properties of bacterial cellulose also allow for the invention's potential application inside the body or for other medical purposes.

The invention also provides a medical device comprising a Bacterial Cellulose (BC) hybrid material wherein a fiber fixed in a pattern is interwoven with the BC.

In one embodiment, the pattern is comprised of one or more filament fibers arranged in a defined non-random direction.

In another embodiment, the pattern is comprised of twisted fibers and/or yarn made up of twisted fibers arranged in any direction.

In one embodiment, the fiber pattern is added to a container suitable for culturing a bacterium capable of producing BC under conditions suitable for the bacteria to produce BC. A structure such as a scaffold comprised of a yarn or multiple yarns is added to the growth/fermentation container. The fiber or yarns comprised of multiple fibers are fixed above, or on the oxygenated side of, the media in a defined pattern, direction or combination of directions. The yarn or yarns are thus incorporated into the BC nanofiber structure during static fermentation.

In another embodiment the fiber/yarn pattern can be suspended in gel media that also provides suitable conditions for BC growth wherein the BC becomes interwoven with the fibers(s).

In one embodiment the arrangement of the yarns is prefabricated through other textile production methods such as weaving or knitting and then fixed to the 'warping frame,' or structure that holds them in place during static growth.

In another embodiment yarns are arranged directly onto 'warping frame' in single or multiple axes 'weave' pattern.

The scaffold is in one embodiment comprised of a single yarn and fiber type or in another embodiment contains multiple different fibers/yarns.

In another embodiment, the fiber pattern is fabricated prior to the BC growth via mechanical and/or automated fiber placement.

In another embodiment, the fiber pattern is a knitted, woven or nonwoven textile assembled according to any method known to the art prior to being interwoven with BC.

In another embodiment, the fiber pattern is pre-fixed to a substrate.

In another embodiment, the fiber pattern is fixed to a substrate by chemical adhesion.

In another embodiment, the fiber pattern is fixed to a substrate by physical adhesion.

In another embodiment, the fiber pattern is fabricated and/or completed during the BC growth via mechanical and/or automated fiber placement.

In another embodiment, the fiber pattern is fabricated and/or completed during the BC growth via biological means such as co-culture.

In one embodiment, one or more of the yarns are filament yarns including but not limited to untwisted filament, twisted filament, and/or stretch filament. Any other types of filament yarns known in the art can also be used.

In one embodiment, one or more of the yarns are spun yarns including but not limited to carded spun, combed spun, ring spun, open-end spun, airjet spun, wrap spun. Any other types of spun yarns known in the art can also be used.

In another embodiment, one or more of the yarns are a woolen yarns.

In another embodiment, one or more of the yarns are worsted yarns.

In another embodiment, one or more of the yarns are braided yarns.

In another embodiment, the fibers comprising one or more of the yarns are transparent.

In another embodiment, one or more of the fibers/yarns are conductive.

In another embodiment, one or more of the fibers/yarns are biocompatible.

In another embodiment, one or more of the fibers are ingestible.

In another embodiment, one or more of the fibers are edible.

In another embodiment, the fibers in one or more of the yarns comprise a natural cellulose-based or protein-based material.

In another embodiment, the natural cellulose-based material is selected from the group consisting of cotton, linen, flax, sisal, ramie, hemp, kenaf, jute, bamboo, banana, pineapple, kapok, and combinations thereof. Any other natural cellulose fibers known in the art can also be used.

In another embodiment, the natural protein-based material is selected from the group consisting of wool, silk, angora, cashmere, mohair, alpaca, milk protein, spider silk, and soy protein and combinations thereof.

In another embodiment, the fibers comprise a polymeric material. In another embodiment, the polymeric material is cellulose acetate, nylon, rayon, modacrylic, olefin, acrylic, polyester, polylactic acid, polylactic-co-glycolic acid (PLGA), polyurethane, aramid (e.g. KEVLAR®), or ultra-high molecular weight polyethylene, (e.g. SPECTRA® or DYNEEMA®). In another embodiment, the fibers comprise carbon (e.g., carbon fiber, nanotubes) or glass (e.g., fiberglass), graphite, or graphene material.

In another embodiment, the fibers comprise of or contain metal material such as aluminum, steel, silver, gold, copper.

In another embodiment, the composition further comprises a resin, which is selected from the group consisting of biodegradable resin, water-soluble resin, natural resin, plant-based resin and non-toxic resin.

The invention also provides a device for preparing a bacterial cellulose (BC) hybrid material, the device comprising of: a container, e.g., a liquid tight container, suitable for culturing bacterium capable of producing cellulose in a suitable medium under conditions to produce BC; and a structure for containing and/or fixing a fiber or multiple fibers in a pattern such that the fiber is interwoven with the BC.

In one embodiment, the structure comprises a frame whereupon fiber pattern is arranged directly in single or multiple axes according to defined pattern.

In another embodiment, the structure comprises a frame whereupon a fiber pattern that is a knitted, woven or nonwoven textile assembled according to any method known to the art can be fixed and interwoven with BC.

In another embodiment, the structure enables a fiber pattern that is fabricated via mechanical and/or automated fiber placement to be interwoven with BC.

In another embodiment, the structure further comprises a system for fabricating or completing the fiber pattern during the BC growth.

In another embodiment, the container is further suitable for co-culturing the bacterium with other microorganisms.

In one embodiment, the structure comprises a base with fixed or adjustable pegs and/or raised supports. The cross section and height of the pegs/supports can be adjusted according to desired design/placement of scaffold within BC matrix.

Any bacterium known to produce BC can be used including but not limited to *Komagataeibacter rhaeticus, Acetobacter xylinum*, or genetically modified versions of a BC-secreting genus.

Any culture medium known in the art to support the selected bacteria can be used. It could be pure or have other fibers incorporated into it.

The hybrid material could be bleached or dyed, dried pure, plasticized using any commercially available plasticizers such as glycerol or impregnated with resin to form a composite.

FIGURES

The invention is described herein with reference to the accompanying drawings. It is to be understood that in some instances, various aspects of the invention may be shown exaggerated or enlarged to facilitate an understanding of the invention.

DETAILED DESCRIPTION

For clarity of disclosure, and not by way of limitation, the detailed description of the invention and process for producing it are divided into the subsections set forth below.

"Pattern", in reference to the pattern of fibers is a non-random and intentional arrangement of fibers in one, multiple or a combination of directions. In an embodiment, a pattern of fibers comprises a mesh of fibers, such as a mesh of yarn, which can be woven, knitted, or the like.

1. Warping Frame and Scaffold Preparation

The purpose of the warping frame is to provide support to the scaffold or matrix of yarns during scaffold assembly as well as during fermentation stage and hybrid material production. The warping frame is composed of a base with fixed or adjustable pegs and/or raised supports.

Figure 1:
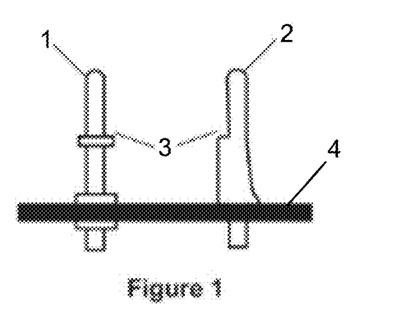
FIG. 1 depicts two examples of warping frame support pegs.
Figure 2:
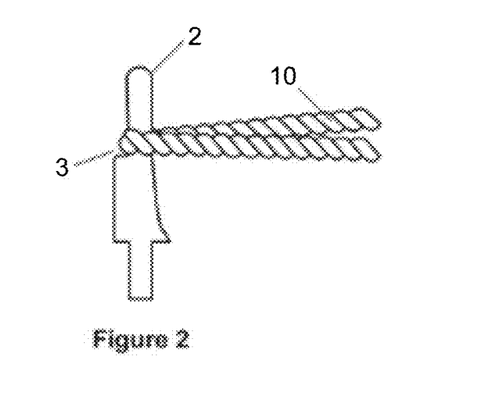
FIG. 2 depicts an example of spun yarns held in place on a warping frame support peg at a notch.

FIG. 1 shows examples of two embodiments of pegs 1, 2. Peg 1 depicts a round peg that is fixed to the base 4 with nut and bolt. Peg 2 depicts a laser cut peg with a rectangular cross section, which is fixed with glue to the base 4. The cross section and height of the pegs/supports 1, 2 can be adjusted according to desired design/placement of scaffold within BC matrix. What is important is that a yarn or multiple yarns can be easily fixed in one or more places 3 on the support 1, 2. FIG. 2 depicts one embodiment of a spun yarn 10, or yarn composed of twisted fibers, fixed to a preferred peg embodiment 2 where a notch 3 holds the yarn 10 in place.

Figure 3:
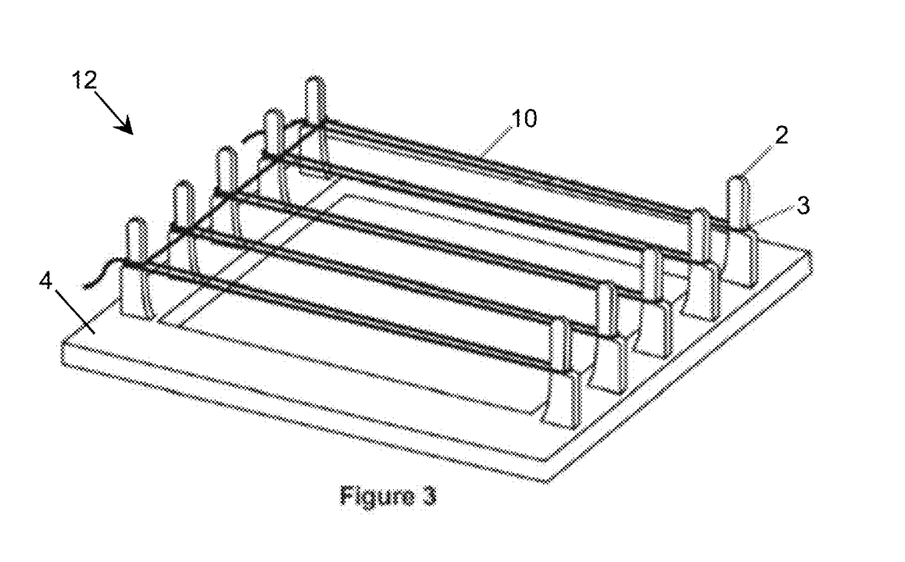
FIG. 3 depicts an angled view of one embodiment of an assembled warping frame with multiple support pegs and an example of applied single yarn scaffold.

FIG. 3 shows one embodiment of an assembled warping frame 12 with multiple support pegs 2 with yarn 10 fixed at the notch 3 in each peg. The yarn 10 is stretched between the notches 3 of pegs 2 to be under tension so that the yarn 10 does not hang down between pegs 2. As a result, the yarn 10 forms a two-dimensional mesh located in a single plane at an elevation above the base 4 corresponding to the elevation of the notches 3.

Figures 4, 5, 6:
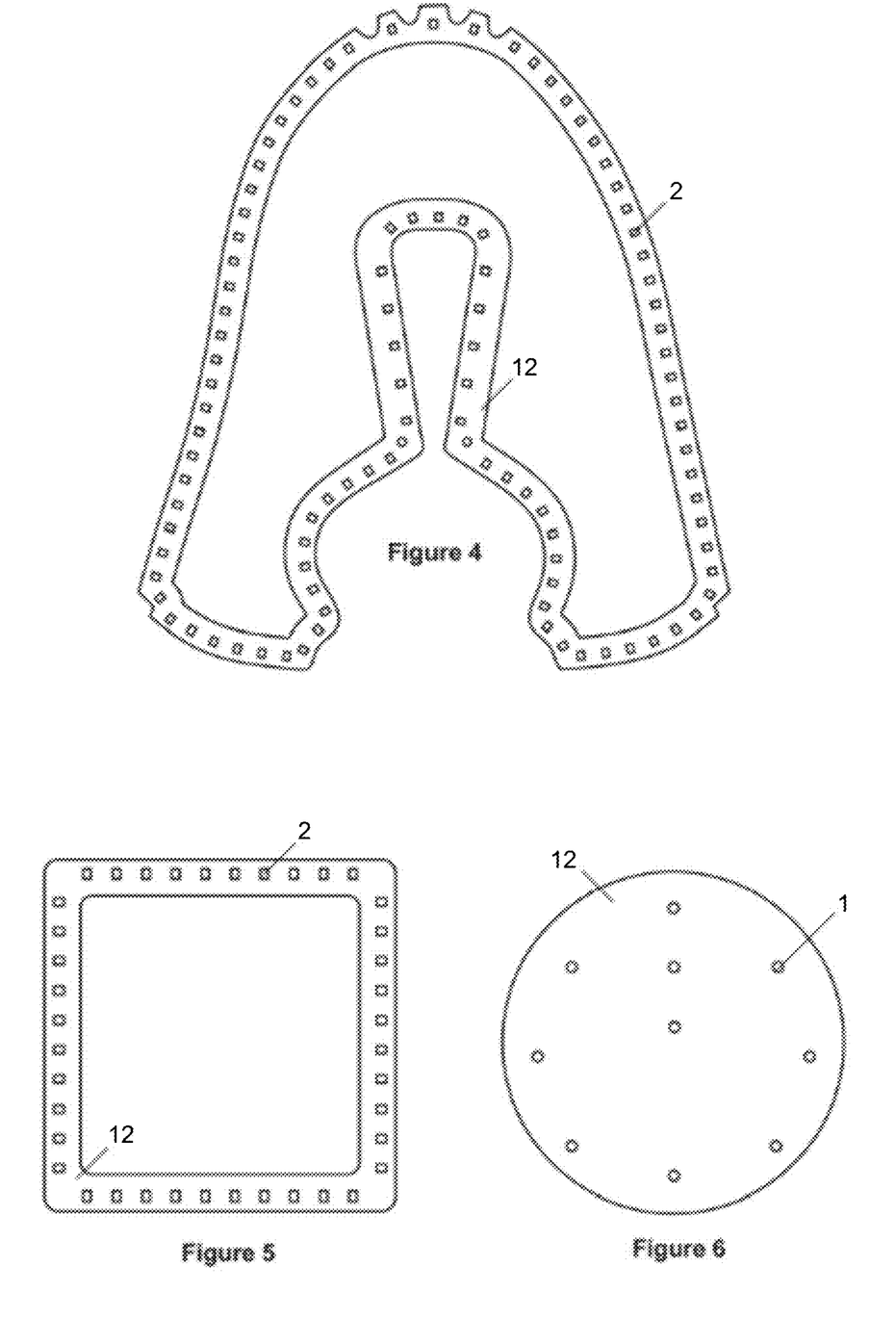
FIG. 4 depicts an example of a warping frame with an irregular shape and rectangular pegs.
FIG. 5 depicts an example of a warping frame with a square shape and rectangular pegs.
FIG. 6 depicts an example of a warping frame with a circle shape, and round pegs.

FIG. 4 depicts an example of a warping frame 12 with an irregular shape and rectangular pegs 2. FIG. 5 depicts an example of a warping frame 12 with a square shape and rectangular pegs 2. FIG. 6 depicts an example of a warping frame 12 with a circle shape, and round pegs 1. There is no limit in shape, size or positioning of base plate and pegs for warping frame embodiments.

The material composition of one warping frame 12 embodiment is acrylic.

In another embodiment, stainless steel is used.

The only limiting factor of the material composition of the warping frame 12 is it should be as inert as possible as to not corrode, rust or react with the liquid chemical composition of the media or material processing solutions such as but not limited to NaOH solution, bleach, or solvents. The material should also not be harmful to living organisms such as bacteria or fungi. Also for many sterilization and finishing treatments it may need to withstand high heats.

Yarn 10 is applied to the warping frame 12 by hand in one embodiment but in other embodiments by machine, robotic arm or automated thread placement mechanism.

In another embodiment, the fibers comprising the yarn are transparent.

In another embodiment, the yarn is conductive.

In another embodiment, the fibers comprise a natural cellulose-based or protein-based material.

In another embodiment, the natural cellulose-based material is selected from the group consisting of cotton, linen, flax, sisal, ramie, hemp, kenaf, jute, bamboo, banana, pineapple, kapok, and combinations thereof. Any other natural cellulose fibers known in the art can also be used.

In another embodiment, the natural protein-based material is selected from the group consisting of wool, silk, angora, cashmere, mohair, alpaca, milk protein, spider silk, and soy protein and combinations thereof.

In another embodiment, the fibers comprise a polymeric material. In another embodiment, the polymeric material is cellulose acetate, nylon, rayon, modacrylic, olefin, acrylic, polyester, polylactic acid, polylactic-co-glycolic acid (PLGA), polyurethane, aramid (e.g. KEVLAR®), or ultra-high molecular weight polyethylene, (e.g. SPECTRA® or DYNEEMA®). In another embodiment, the fibers comprise carbon (e.g., carbon fiber) or glass (e.g., fiberglass).

Figure 7:
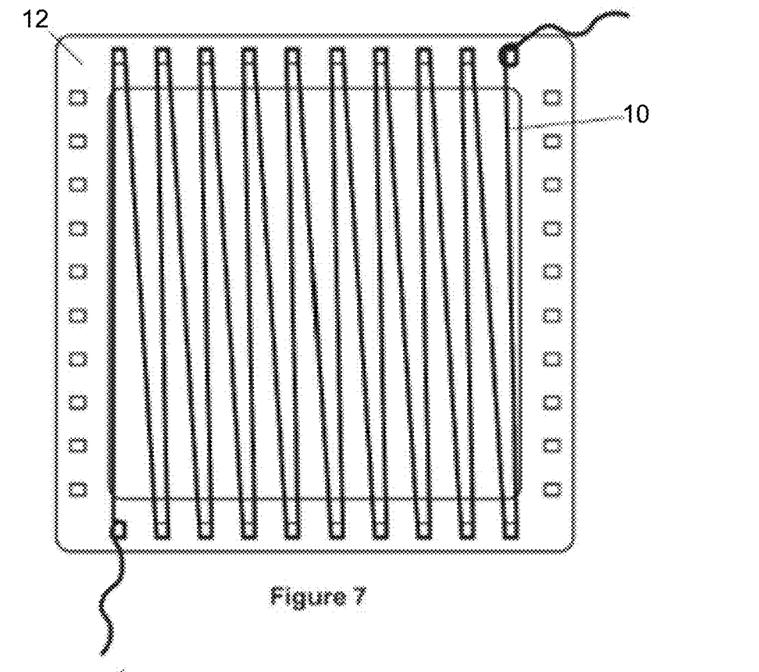
FIG. 7 depicts an example of an embodiment where a single yarn is arranged directly on the warping frame.
Figure 8:
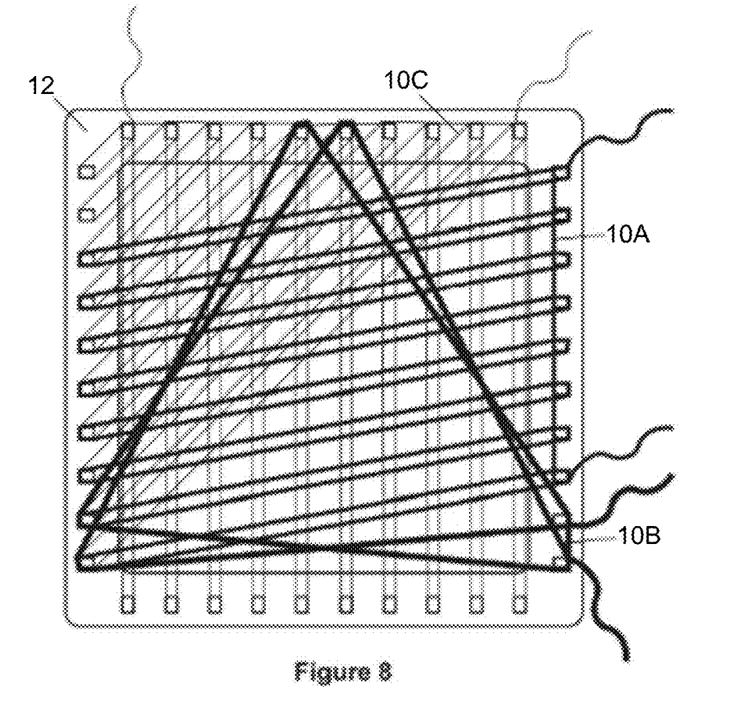
FIG. 8 depicts an example of an embodiment where a multiple different yarns are arranged directly on the warping frame.

The scaffold could be comprised of a single yarn and fiber type or could contain multiple different yarns in a single hybrid material. The arrangement of the yarns could be prefabricated through other textile production methods such as weaving or knitting and fixed to 'warping frame' or can be arranged directly onto 'warping frame' in single or multiple axes weave pattern. FIG. 7 depicts an example of an embodiment where a single yarn 10 is arranged directly on the warping frame 12. FIG. 8 depicts an example of an embodiment where a multiple different yarns 10A, 10B, 10C are arranged directly on the warping frame 12.

As yarns often contain contaminants and/or other microbes or can easily become contaminated during handling. For this reason, it is important to sterilize the frame and yarn after yarn is applied to the frame, and/or prevent pre-sterilized elements from being contaminated during assembly. Sterilization method depends on the composition of the warping frame as well as the yarn used. Sterilization methods include but are not limited to soaking in ethanol or bleach solution, dry heat, autoclave, exposure to UV light, or other chemical sterilization methods.

2. Bacteria and Culture Media for BC Production

Methods are provided herein for producing bacterial cellulose (BC). In one embodiment, the method comprises providing a bacterium wherein the bacterium is a bacterial cellulose-producing bacterium; providing a bacteria nutritional medium; culturing the bacterium in the bacteria nutritional medium under conditions to produce BC.

Many strains of bacteria that synthesize cellulose can be used to synthesize BC including but not limited to *Komagataeibacter rhaeticus, Acetobacter xylinum*, or genetically modified versions of BC secreting genus. In a preferred embodiment, *Komagataeibacter rhaeticus* is used.

In one embodiment, *Acetobacter xylinum*, ATCC 23769, can be used (American Type Culture Collection (ATCC), Manassas, Va.).

In other embodiments, the following can be used.
*Gluconacetobacter hansenii* ATCC 53582
*Gluconacetobacter xylinus* ATCC 23767
*Acetobacter pasteurianus* ATCC 10245
*Acetobacter liquefaciens* ATCC 14835

Any culture medium known in the art to support the selected bacteria can be used. For example, culture media that can be used can consist of 5-50 g/l, of one or more carbon sources (e.g., stachyose, raffinose, glucose, sucrose, fructose, mannitol, galactose, maltose), 5 g/L yeast extract and 5 g/L tryptone. In one embodiment, 25 g/L is used. Any small sugar known in the art can also be used. For example, HS-glucose media for culturing *Komagataeibacter rhaeticus* as described in Florea et al., Engineering control of bacterial cellulose production using a genetic toolkit and a new cellulose-producing strain. PNAS 113 (24), May 2016. In a preferred embodiment, media is prepared using a solution of pure coconut water with 1% volume of Aspall's organic Cyder Vinegar. The coconut water media is sterilized in microwave as it cannot be autoclaved.

In one embodiment a liquid medium is used, in another embodiment the growth medium may be a gel.

3. Growth/Fermentation Container Design and Preparation

Details are provided here for building a device for preparing a bacterial cellulose (BC) hybrid material, the device comprising of: a container suitable for culturing bacterium capable of producing cellulose in a suitable medium under conditions to produce BC; and a structure for containing and/or fixing a fiber or multiple fibers in a pattern such that the fiber is interwoven with the BC.

Figure 9:
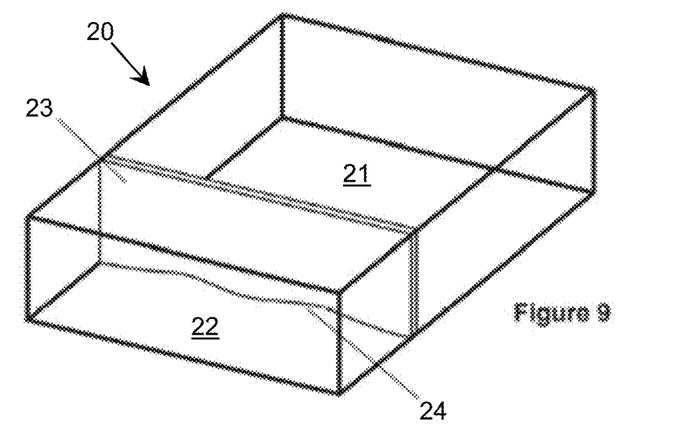
FIG. 9 is a perspective view of one embodiment of a fermentation container.
Figure 10:
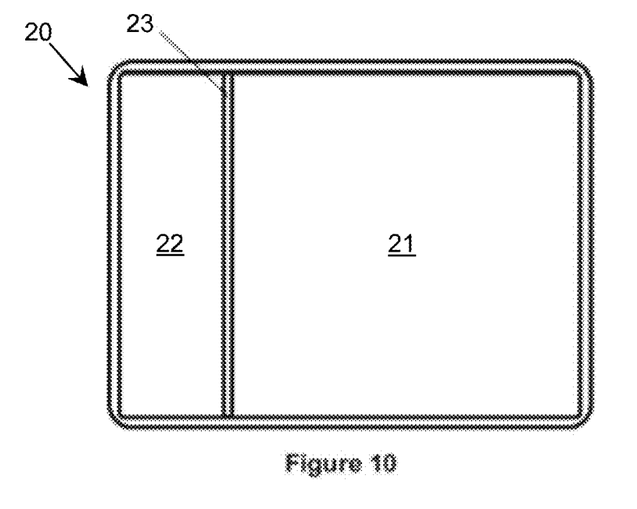
FIG. 10 is the top view of one embodiment of a fermentation container.
Figure 11:
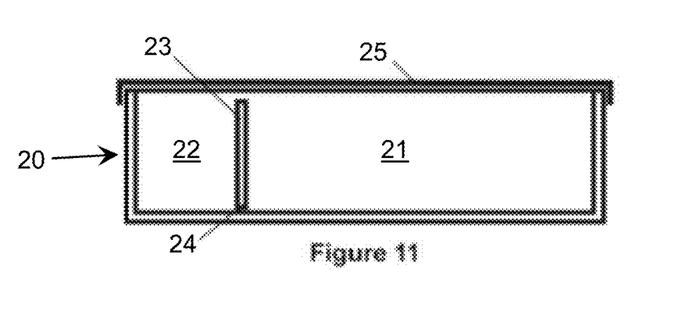
FIG. 11 is the side view of one embodiment of a fermentation container.

The fermentation container should be made out of an inert and easily sterilized material. In a preferred embodiment, the container is clear glass to allow for better monitoring of fermentation/growth but in other embodiments is opaque. FIGS. 9-11 show top (FIG. 10), side (FIG. 11) and perspective (FIG. 9) views of one embodiment of a fermentation container 20. Import features include two separate sections, a material production compartment 21 and a media addition compartment 22. These are separated by a divider 23 that prevents liquid from flowing easily between the areas except for through a narrow opening 24 at the bottom of the divider. The shape of the container and subsequent compartments can be changed to suit desired size and shape of hybrid pellicle. The pellicle will take on the shape of the material production compartment 21. Container 20 has a lid 25 to protect from contamination by other organisms during fermentation but that allows or promotes oxygen flow to the culture.

In one embodiment, a paper towel is used as a lid.

In another embodiment, a sterile cloth is used as a lid.

In another embodiment, lid is sealed onto container with tube inserted to control gas flow in and out of the container.

In another embodiment, container is to be sterilized prior to growth. Sterilization methods include but are not limited to soaking in ethanol or bleach solution, dry heat, autoclave, exposure to UV light, or other chemical sterilization methods. Most effective sterilization method should be determined based on material composition of the container.

4. Hybrid Textile-BC Pellicle Production

Figure 12:
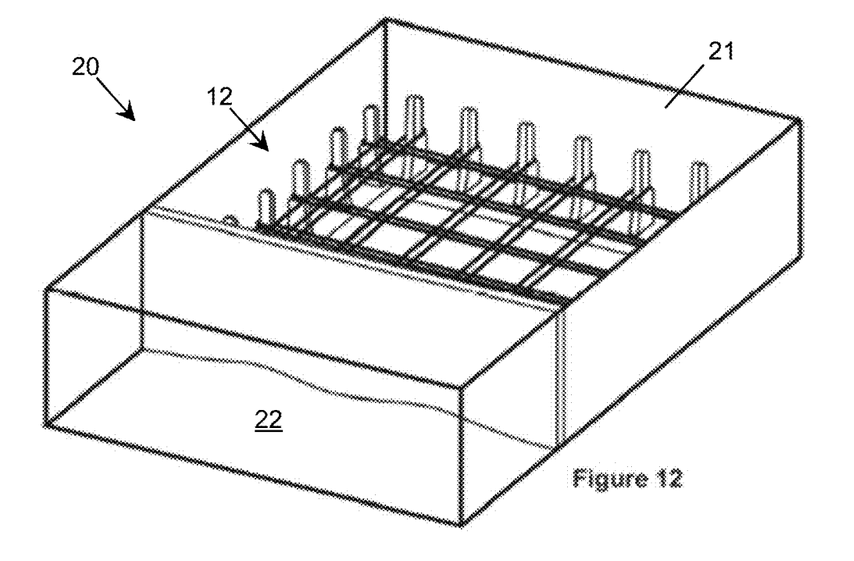
FIG. 12 shows perspective view of positioning of warping frame placement in fermentation container.
Figure 13:
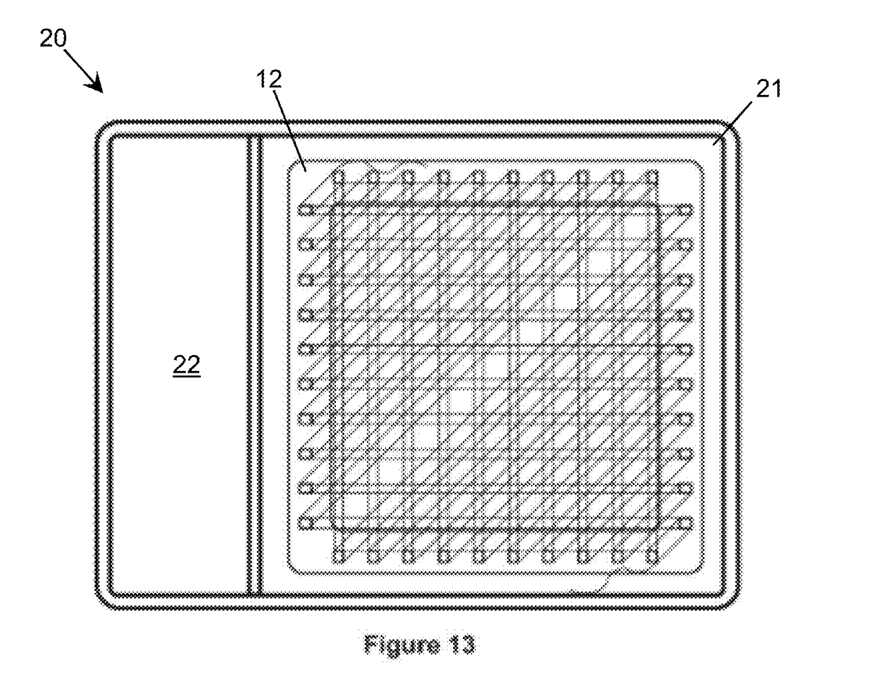
FIG. 13 shows top view of positioning of warping frame placement in fermentation container.
Figure 14:
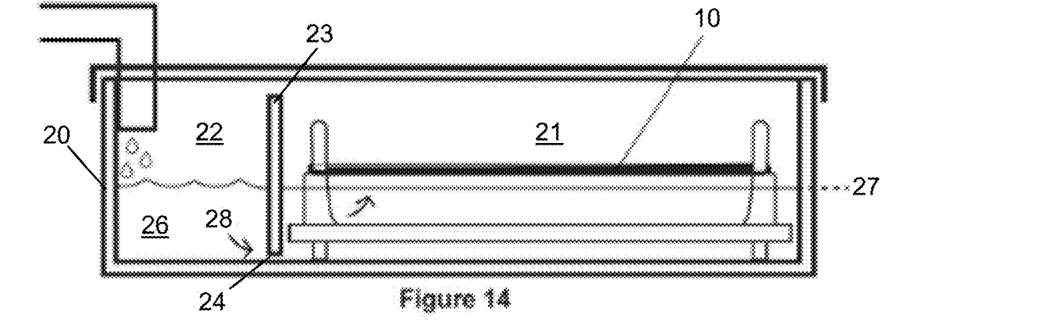
FIG. 14 is a side view of the of fermentation container with inoculated media and warping frame in starting setup.

FIGS. 12 and 13 show top (FIG. 13) and perspective (FIG. 12) views of how the assembled scaffold/warping frame 12 is placed within fermentation container 20. FIG. 14 shows the side view of set up fermentation container 20 where number 10 indicates the yarn scaffold and number 26 indicates the media. Once warping frame 12 is in place in the material production compartment 21, prepared media and starter bacteria culture 26 are added slowly into media addition compartment 22. As indicated by arrow 28, the media and bacteria 26 travel through the gap 24 at the bottom of the barrier 23 until liquid media equalizes and reaches the predetermined fill line 27 in all compartments. It is important that the container 20 remains level throughout full fermentation stage.

Figure 15:
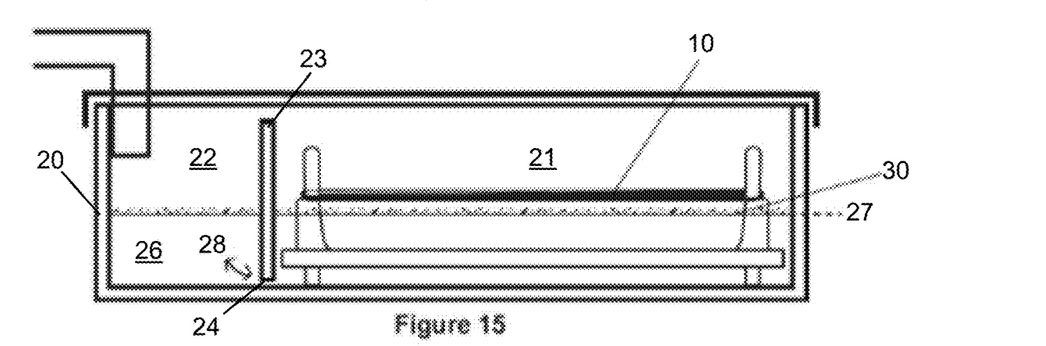
FIG. 15 is a side view of the of fermentation container and pellicle growth after 2-4 days.

FIG. 15 shows BC pellicle growth after 2-4 days, number 30 indicates visible layer of BC. Arrow 28 indicates how media 26 in all compartments remains at equilibrium during fermentation.

Figure 16:
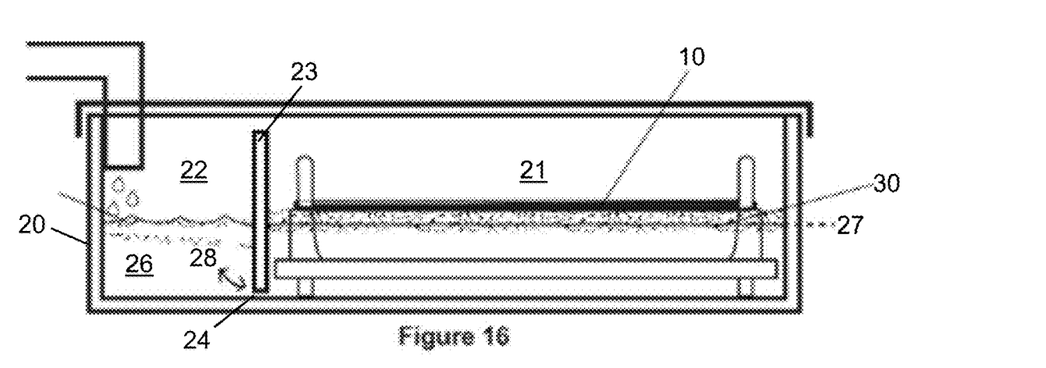
FIG. 16 is a side view of the of fermentation container and pellicle growth after 4-8 days.

FIG. 16 shows BC pellicle 30 after 4-8 days when surface of the pellicle reaches the scaffold and starts to incorporate the yarns 10 into its structure.

Media 26 is continually added in small amounts to media addition compartment 22 throughout fermentation so that media 26 remains at fill line 27 in equilibrium throughout entire fermentation. This provides conditions for the pellicle 30 in the material production area 21 to grow evenly with minimal imperfections.

A pellicle also forms in the media addition compartment 22 but usually will grow unevenly or in layers as the addition of media disturbs its growth.

In another embodiment, media 26 is applied in the form of a fine mist to the top (or oxygen exposed side) of the growing pellicle 30 to help stimulate growth.

Figure 17:
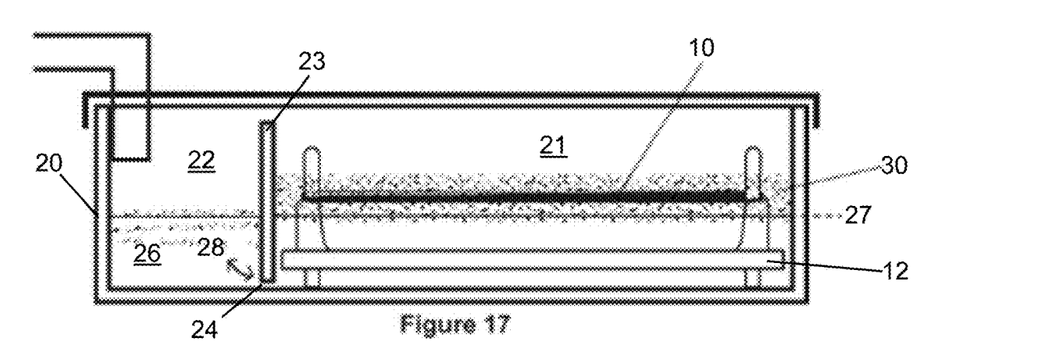
FIG. 17 is a side view of the fermentation container and pellicle growth after 7-15 days, or when material is fully-grown.

FIG. 17 shows final BC-textile hybrid pellicle 30 after yarns 10 are fully incorporated, usually within 7 to 15 days depending on growth conditions. Hybrid pellicle 30 is still fixed in place on warping frame 12 at the end of this phase. In one embodiment the hybrid pellicle 30 is removed gently from the warping frame before post processing. In another embodiment it remains on the frame for post processing.

Figure 18:
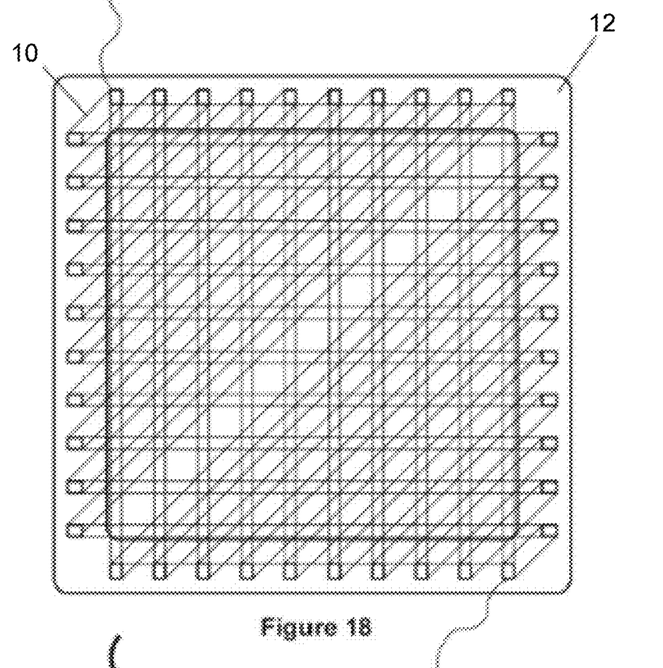
FIG. 18 shows the top view of one embodiment of a scaffold fixed to a warping frame before being added to growth/fermentation container for BC production.
Figure 19:
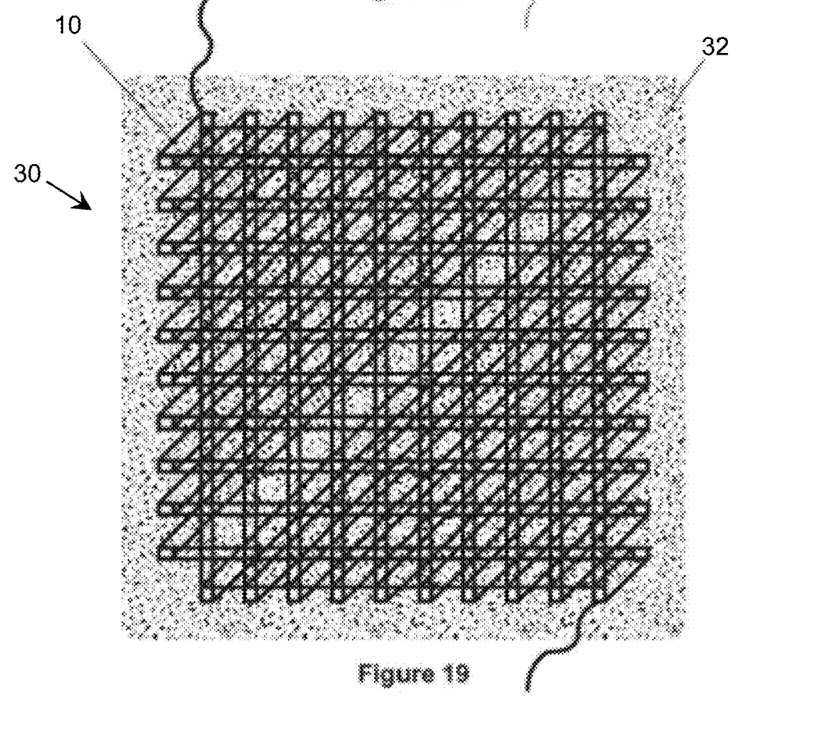
FIG. 19 shows the top view of fully grown BC-textile hybrid pellicle removed from growth/fermentation container.

When removed from the frame 12, both BC fibers and fibers characterizing the yarns might shift slightly but yarns 10 should still remain completely or partly fixed within the BC matrix. FIG. 18 shows the top view of one embodiment of a scaffold comprised of a yarn 10 fixed to a warping frame 12 before being added to growth/fermentation container for BC production. FIG. 19 shows the top view of the fully grown BC-textile hybrid pellicle 30 removed from growth/fermentation container and warping frame, number 10 indicates area where yarn fibers are concentrated and 32 denotes BC growth through the openings between the yarns and fibers of the yarns and where growth was not inhibited by the yarns, the shape of the container, or other means.

Figure 20:
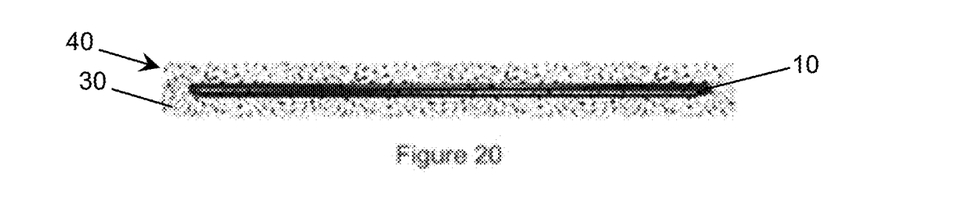
FIG. 20 shows a cross section of one embodiment of the BC-textile hybrid material (wet) where yarns are concentrated at the midpoint of the pellicle.

FIG. 20 shows a cross section of one embodiment of the BC-textile hybrid material 40 (wet) where yarns 10 are concentrated at the midpoint of the BC pellicle 30.

Figure 21:
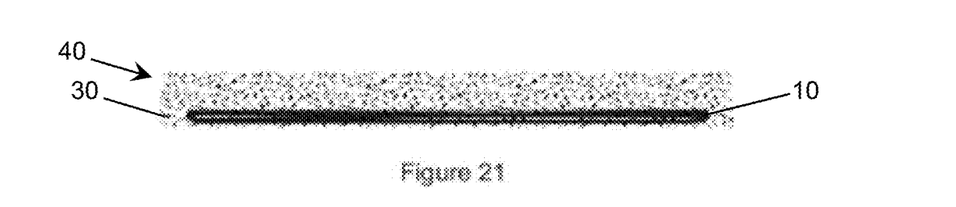
FIG. 21 shows a cross section of one embodiment of the BC-textile hybrid material (wet) where yarns are concentrated at bottom of the pellicle.

FIG. 21 shows a cross section of one embodiment of the BC-textile hybrid material 40 (wet) where yarns 10 are concentrated at bottom of the pellicle 30.

Figure 22:
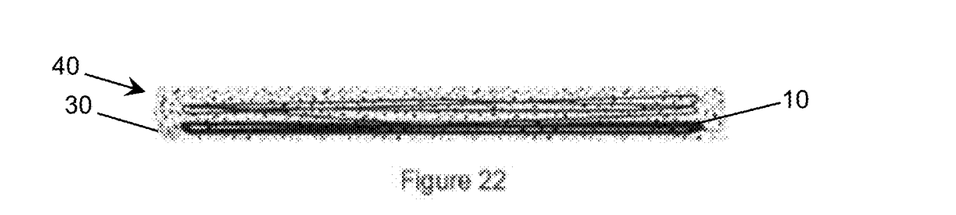
FIG. 22 shows a cross section of one embodiment of the BC-textile hybrid material (wet) where yarns are spread throughout thickness of the pellicle.

FIG. 22 shows a cross section of one embodiment of the BC-textile hybrid material 40 (wet) where yarns 10 are spread throughout thickness of the pellicle 30. In an embodiment, the yarns 10 are multiple different yarns as shown in FIG. 8.

Figure 23:
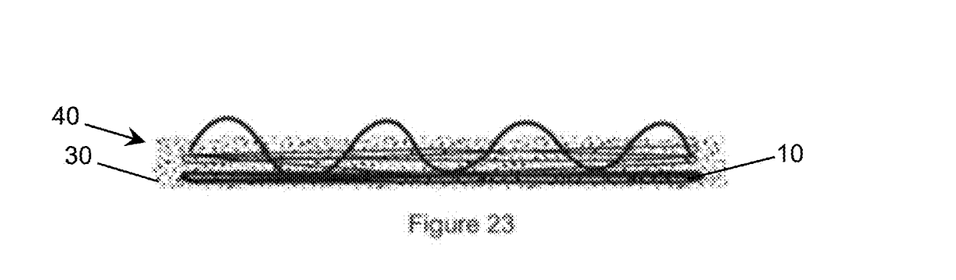
FIG. 23 shows a cross section of one embodiment of the BC-textile hybrid material (wet) where yarns are spread throughout thickness of the pellicle, and parts of the yarn extend outside of the pellicle.

FIG. 23 shows a cross section of one embodiment of the BC-textile hybrid material 40 (wet) where yarns 10 are spread throughout thickness of the pellicle, and parts of the yarn extend outside of the pellicle 30.

Wash BC crude pellicle successively with water and 1% (w/v), aqueous NaOH, and then remove all microbial product contaminants by deionized water (BC wet pellicle).

The hybrid material could be bleached or dyed, dried pure, plasticized using any commercially available plasticizers such as glycerol or impregnated with resin to form a composite.

Remove water from the BC either by pressing, air dry, oven dry or freeze dry (for BC film), or combination there of.

In one embodiment the material is impregnated with resin.

In another embodiment, the resin is transparent.

In another embodiment, the resin is selected from the group consisting of natural resin, plant-based resin and non-toxic resin.

In another embodiment, the resin is biodegradable.

In another embodiment, the resin is water-soluble.

In another embodiment, the natural or plant-based resin is a soy-based resin.

In another embodiment, the resin is a petroleum-based resin.

In another embodiment, the petroleum-based resin is an epoxy, vinyl, or unsaturated polyester-based resin.

In another embodiment, the resin is polyethylene oxide (PEO).

In another embodiment, the resin is polyvinyl alcohol (PVA).

In another embodiment, the resin is polyhydroxy alkanoate (PHA).

Example Protocol

Listed below is an example protocol for the production of one embodiment of the invention.

Media solution is prepared using pure coconut water with 1% volume of Aspall's organic Cyder Vinegar. Media is sterilized by microwaving in a covered glass container (but not sealed). For 500 ml of solution it is heated in the microwave for 6 minutes then allowed to cool (still covered) naturally to room temperature (22-25 degrees Celsius).

Bacteria Used is *Komagataeibacter rhaeticus*.

Starter culture is prepared in small sterilized glass jar (5 cm diameter) by adding bacteria to about 3 cm depth of sterilized media solution. It is covered with a paper towel and culture is left static at 22 degrees C. for about 7 days or at least until a pellicle of about 6 mm is formed at the surface.

Construct warping frame using laser cut acrylic base and support pegs. See FIG. 2 for shape of example peg. In this example, 3 mm thick sheet of clear acrylic is used for the pegs and 5 mm clear acrylic for the base. Each peg is identical with a height of 40 mm and notch at height of 25 mm. Base is 150 mm×150 mm square with 40, 3 mm by 4 mm, rectangular holes, 10 on each side of the square at a distance of 9 mm apart. 40 pegs are secured to the based by insertion into the holes and fixed perpendicular to the base using dichloromethane. See FIG. 18 for reference of peg spacing.

Apply 16/2 organic cotton yarn directly to the warping frame by fixing yarn to each peg at its notch. The thread is tied off at first and last peg to avoid unraveling. See FIG. 18 for reference of yarn arrangement in this example.

See FIGS. 9-11 as reference for growth/fermentation container design. Whereas the outside of the container is made of clear vacuum formed plastic and the divider laser cut acrylic.

The assembled frame and container are both sterilized by short soak in ethanol and air dried (covered) until ethanol fully evaporates.

See FIGS. 12-13 as reference for how the frame is placed into the growth container.

The entire contents of starter culture jar are carefully (to avoid contamination) added to the media addition compartment of the container and sterilized media is added to the same side slowly until equilibrium at fill line is met (see FIG. 14). In this example the fill line is set at a height of 23 mm or 2 mm below yarn scaffold.

Container is covered with a paper towel and left static on a level surface. Incubate at 22-25 degrees Celsius. Throughout fermentation process the media level will drop and it is imperative it is monitored and media be added (to media addition compartment only) throughout growth so media level stays at equilibrium at fill line (number 27 in FIGS. 14-17).

Allow fermentation to occur for 10-15 days or until yarn is fully incorporated into (e.g., embedded within) the BC and hybrid pellicle is about 6 mm thick.

Remove frame from container but leave pellicle on warping frame.

Wash BC crude pellicle successively with water and 1% (w/v), aqueous NaOH at room temperature C. for 15 min, and then remove all microbial product contaminants by deionized water (BC wet pellicle).

Then soak pellicle in water and 5% (w/v), aqueous glycerol solution for 8 hours.

Remove pellicle carefully from frame and press out excess water by placing it between 2 sheets of fine metal mesh and wooden boards to which even pressure is applied. Let further air dry until about 2 mm thick. Place between two sheets of wax paper, surround with paper towel and place between 20 mm plywood boards. Apply even pressure using nuts and bolts to clamp boards together and leave until hybrid material is fully dried.

What is claimed is:

1. A composition comprising:
    a sheet of bacterial cellulose (BC) including a first outer surface and a second outer surface opposite the first outer surface; and
    a two-dimensional yarn mesh formed of yarn, wherein the yarn mesh is stretched and completely embedded within the BC sheet in a single plane parallel to and distanced from the first and second outer surfaces of the BC sheet, wherein the yarn mesh includes openings through which the BC extends uninhibited by the yarn mesh, and wherein the openings are distributed throughout a lateral area of the yarn mesh.

2. The composition of claim 1, wherein the yarn comprises one or more filament yarns.

3. The composition of claim 1, wherein the yarn comprises one or more spun or twisted yarns.

4. The composition of claim 1, wherein the yarn is a natural yarn selected from a group consisting of: silk; cotton; flax; and wool.

5. The composition of claim 1, wherein the yarn is woven into the yarn mesh.

6. The composition of claim 1, wherein the yarn is knitted into the yarn mesh.

7. The composition of claim 1, wherein the BC sheet includes only a single yarn mesh embedded therein.

8. The composition of claim 1, further comprising a two-dimensional fiber mesh, wherein the fiber mesh is embedded and stretched within the BC in a plane parallel to the yarn mesh.

9. The composition of claim 1, wherein the composition further comprises a resin.

10. The composition of claim 9, wherein the resin is selected from a group consisting of: a biodegradable resin; a water-soluble resin; and a natural resin.

11. The composition of claim 9, wherein the resin is selected from a group consisting of: polyethylene oxide (PEO); polyvinyl alcohol (PVA); and
    polyhydroxy alkanoate (PHA).

12. A composition comprising:
a sheet of bacterial cellulose (BC) having a first outer surface and a second outer surface located opposite the first outer surface; and
a two-dimensional pattern of fibers embedded within and extended throughout the BC sheet, wherein the pattern of fibers is stretched and completely embedded within the BC sheet in a single plane substantially parallel to and distanced from the first and second outer surfaces of the BC sheet, wherein the pattern of fibers defines a pattern of openings through which the BC extends uninhibited by the pattern of fibers from a first side to a second side of the pattern of fibers.

13. The composition of claim 12, wherein the pattern of fibers comprises a mesh.

14. The composition of claim 12, wherein the pattern of fibers is formed of yarn.

15. The composition of claim 12, wherein the pattern of fibers is concentrated at a midpoint of the BC sheet.

16. The composition of claim 12, further comprising a resin embedded within the BC sheet.

17. A plastic biopolymer formed of the composition of claim 12.

18. A wearable accessory at least partially formed of the composition of claim 12.

19. A wearable article comprising:
a hybrid material forming at least one surface of the wearable article, the hybrid material comprising:
a sheet of bacterial cellulose (BC) having a first outer surface and a second outer surface located opposite the first outer surface; and
a two-dimensional pattern of fibers embedded within and extended throughout the BC sheet, wherein the pattern of fibers is stretched and completely embedded within the BC sheet in a single plane substantially parallel to and distanced from the first and second outer surfaces of the BC sheet, wherein the pattern of fibers defines a pattern of openings through which the BC extends uninhibited by the pattern of fibers from a first side to a second side of the pattern of fibers.

20. The wearable article of claim 19, wherein the article is one of: an article configured to be worn on a foot, an article of clothing, or a wearable accessory.

* * * * *